(12) United States Patent
Hui et al.

(10) Patent No.: US 6,436,659 B1
(45) Date of Patent: Aug. 20, 2002

(54) BIOLOGICAL INDICATOR FOR STERILIZATION PROCESSES WITH DOUBLE BUFFER SYSTEM

(75) Inventors: Henry K. Hui, Laguna Niguel; Leslie A. Feldman, Calabasas Hills; Richard A. Gorham, Laguna Beach, all of CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

(21) Appl. No.: 09/699,728

(22) Filed: Oct. 27, 2000

(51) Int. Cl.[7] .............................. C12Q 1/22; C12Q 1/02; C12M 1/34
(52) U.S. Cl. ..................... 435/31; 435/29; 435/287.4; 435/288.1
(58) Field of Search ..................... 435/31, 29, 287.4, 435/288.1

(56) References Cited

U.S. PATENT DOCUMENTS

| | | |
|---|---|---|
| 4,291,122 A | 9/1981 | Orelski |
| 4,743,537 A | 5/1988 | McCormick et al. |
| 4,914,034 A | 4/1990 | Welsh et al. |
| 5,073,488 A | 12/1991 | Matner et al. |
| 5,552,320 A | 9/1996 | Smith |
| 5,601,998 A | 2/1997 | Mach et al. |
| 5,866,356 A | 2/1999 | Albert et al. |
| 5,968,807 A | 10/1999 | Kaiser |

*Primary Examiner*—Leon B. Lankford, Jr.
*Assistant Examiner*—Susan D. Coe
(74) *Attorney, Agent, or Firm*—Knobbe, Martens, Olson & Bear, LLP.

(57) ABSTRACT

A method and an apparatus for preventing reversion of the color of an indicator dye in a biological indicator is disclosed. The indicator dye changes color if viable microorganisms are present after sterilization, because acidic byproducts are formed when the microorganisms metabolize the growth medium. It has been found that the dye can change color back to the original color after the completion of the sterilization due to leaching or diffusion of basic impurities into the growth medium. The method and the apparatus employ a dual buffer system with one buffer which operates at high pH to moderate pH fluctuations at the start of the sterilization and a second buffer which operates at low pH to minimize pH fluctuations after the sterilization is complete. Less high pH buffer than low pH buffer is used in order to maximize the speed and sensitivity of the biological indicator.

12 Claims, 3 Drawing Sheets

BIOLOGICAL INDICATOR FOR STERILIZATION PROCESSES WITH DOUBLE BUFFER SYSTEM

BACKGROUND OF THE INVENTION

1. Field of the Invention

This invention relates to a double buffer system for preventing color reversion of the pH indicator dye which is used to detect bacterial growth in a biological indicator for monitoring the efficacy of a sterilization process.

2. Description of the Related Art

A variety of sterilization systems are used to sterilize medical devices in hospitals and other medical facilities. Steam, heat, ethylene oxide, and hydrogen peroxide are commonly used as sterilants. The STERRAD® sterilization system, available from Advanced Sterilization Products of Irvine, Calif., is an exemplary sterilization system which utilizes a combination of hydrogen peroxide and plasma to sterilize medical equipment.

In all of these sterilization processes, biological indicators are commonly used to confirm the effectiveness of the sterilization process. The biological indicators generally include a carrier which has been inoculated with spores or other microorganisms. The effectiveness of the sterilization is assessed by determining whether subjecting the biological indicator to the sterilization cycle destroys all of the microorganisms on the carrier.

The biological indicator is placed into the sterilizer together with the equipment to be sterilized. After the completion of the sterilization process, the biological indicator is removed from the sterilizer, and the carrier is immersed into a sterile culture medium. The culture medium and carrier are incubated for a predetermined time at an appropriate temperature. At the end of the incubation period, an indicator is used to determine whether any microorganisms have survived. If no growth of the microorganisms occurs, it is assumed that the articles in the sterilizer have been properly sterilized. If microorganism growth has occurred, the articles in the sterilizer may not be sterile.

A pH indicating chemical which changes color with a change in pH can be used as an indicator, because acidic byproducts are formed when microorganisms metabolize the growth medium. An acidic change in the pH of the growth medium in the biological indicator therefore indicates bacterial growth. Alternatively, the indicator can be, for example, turbidity in the culture medium which results from cell colonies produced by bacterial growth.

In some biological indicators, the microorganisms, the culture medium, and the indicator are packaged in a way which permits the microorganisms, the culture medium, and the indicator to be combined without exposing the biological indicator to the non-sterile surroundings. This type of biological indicator is a "self-contained biological indicator" or SCBI. Use of SCBIs simplify the test process and minimize the chance that external contamination could affect the test results.

McCornick et al. (U.S. Pat. No. 4,743,537), for example, disclose a SCBI having a compartment with a permeable opening which permits the transmission of sterilant gas or steam while preventing the passage of microorganisms into or out of the compartment. The compartment contains a breakable ampoule with a culture medium. Indicating microorganisms are placed on one end of a wick, and the wick is placed in the compartment, with the end of the wick containing the microorganisms away from the media-containing ampoule and adjacent the permeable opening. After the sterilization process, the device is removed from the sterilizer, and the ampoule is broken, releasing the culture medium into the compartment. The device is incubated and examined to determine whether or not microorganism growth has occurred.

The apparatus and the method of the present invention address the previously unrecognized cause of a problem when using biological indicators containing indicator dyes for detecting microbial growth to determine the efficacy of a sterilization process.

SUMMARY OF THE INVENTION

One aspect of the invention involves a method for determining the effectiveness of a disinfection or sterilization process. The method includes providing a carrier with microorganisms on the carrier, exposing the carrier to the disinfection or sterilization process, and incubating the carrier in a growth medium to determine whether the microorganisms grow in the growth medium. The growth medium contains a first buffer with a first $pK_a$, a second buffer with a second $pK_a$, and a pH-sensitive dye. The carrier is incubated in the growth medium after exposure to the disinfection or sterilization process. Growth of the microorganisms in the growth medium generates acid, changing the pH in the growth medium from first pH in a first pH range to a second pH in a second pH range. The first $pK_a$ and said second $pK_a$ are within the first pH range and the second pH range, respectively.

Advantageously, determining whether the microorganisms have grown involves determining whether the pH changes in the growth medium. Preferably, the pH-sensitive dye has a first color in the first pH range and a second color in the second pH range. The determination of whether the microorganisms have grown includes determining whether the dye changes color from the first color to the second color.

Preferably, there is a lower concentration of buffer having a $pK_a$ in the first pH range than buffer having a $pK_a$ in the second pH range. Advantageously, the growth medium is contained in an openable enclosure, and the carrier is incubated in the growth medium by opening the enclosure and immersing the carrier in the growth medium. In an embodiment, the carrier and the growth medium are located in a container covered with a gas or vapor permeable but microorganism impermeable barrier. During the disinfection or sterilization process, a germicide gas or vapor diffuses from outside the container into the container through the barrier.

Advantageously, the microorganism is a biological indicating microorganism for the disinfection or sterilization process. Preferably, the disinfection or sterilization process uses steam, heat, ethylene oxide, hydrogen peroxide, ozone, chlorine dioxide, peracetic acid, performic acid, formaldehyde, glutaraldehyde, ortho-phthalaldehyde, or hypochorite salts as the disinfecting or sterilizing agent.

Another aspect of the invention involves a self-contained biological indicator including a carrier inside a container. The carrier includes viable microorganisms. At least part of the container is transparent, and the container has an opening which is covered with a gas or vapor permeable but microorganism impermeable barrier. At least one openable enclosure is located inside the container. The enclosure contains a culture medium which is capable of supporting growth of the viable microorganisms and a dye which changes color with a change in pH from a first pH range to a second pH range. The enclosure also contains dual buffer system made up of a first buffer having a first $pK_a$ and a second buffer having a second $pK_a$. The first $pK_a$ and said second $pK_a$ are within the first pH range and the second pH range, respectively.

The carrier may be a porous substrate, a non-porous substrate, an absorbent substrate, or a non-absorbent substrate. Advantageously, the gas or vapor permeable but microorganism impermeable barrier is a nonwoven polyolefin. Preferably, the viable microorganism is a biological indicating microorganism for a disinfection or sterilization process. In an embodiment, the openable container is a breakable glass ampoule. Advantageously, the dye is Bromcresol Purple. Preferably, the first buffer includes at least one phosphate salt. In an embodiment, the second buffer includes at least one acetate salt. Preferably, the acetate salt is sodium acetate.

Advantageously, the dual buffer system contains a lower concentration of buffer having a $pK_a$ in the first pH range than buffer having a $pK_a$ in the second pH range. Preferably, the self-contained biological indicator also has a cap with at least one opening above the barrier, so that gas or vapor can diffuse into said container through the hole and the barrier. In an embodiment, the self-contained biological indicator also has a chemical indicator for indicating exposure of the self-contained biological indicator to a disinfection or sterilization process.

Another aspect of the invention involves a culture medium which is capable of supporting growth of viable microorganisms. The culture medium includes a nutrient broth, a dye which changes color with a change in pH from a first pH range to a second pH range, and a dual buffer system. The dual buffer system contains a first buffer having a first $pK_a$ and a second buffer having a second $pK_a$, where the first $pK_a$ and the second $pK_a$ are within the first pH range and the second pH range, respectively.

Advantageously the dye in the culture medium is Bromcresol Purple. Preferably, the first buffer includes at least one phosphate salt. In an embodiment, the second buffer includes at least one acetate salt. In an exemplary embodiment, the acetate salt is sodium acetate. Advantageously, the dual buffer system includes a lower concentration of buffer having a $pK_a$ in the first pH range than buffer having a $pK_a$ in the second pH range.

DETAILED DESCRIPTION OF THE PREFERRED EMBODIMENT

Figure 1:
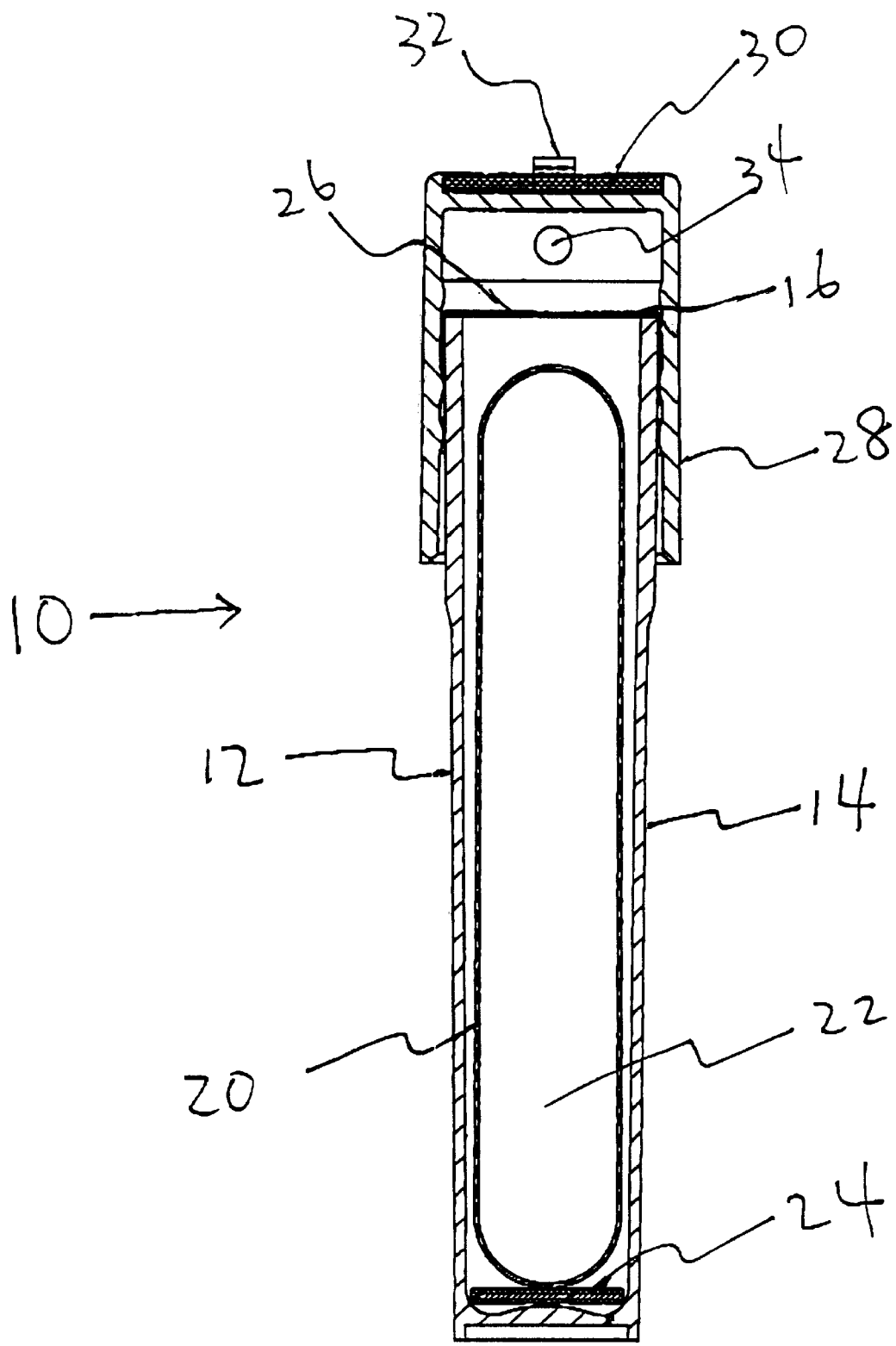
FIG. 1 is a cross-sectional view of a self-contained biological indicator suitable for use with the embodiments of the method of the present invention.

The presence of viable microorganisms in a biological indicator after completion of a sterilization cycle is often determined with a pH indicator, because acidic byproducts are formed when the microorganisms metabolize the growth medium. An acidic shift in the pH in the growth medium is therefore an indication of incomplete sterilization. However, it has been found that pH-raising (basic) contaminants can enter the growth medium after the pH sensitive dye has changed color due to acid generation from bacterial growth. The basic contaminants can unintentionally shift the pH of the growth medium, changing the color of the indicator dye back to its original color so that the indicator color is no longer stable. It has been found that the basic contaminants can sometimes enter the growth medium, for example, by leaching or diffusion out of the plastic material from which many self-contained biological indicators are made.

The color reversion of the dye would falsely indicate that no microorganism growth had occurred. If an observer simply looked at the biological indicator at the end of the incubation period, the observer would believe that there had been no bacterial growth, because the dye would have reverted to its original color. Further, if the observer monitored the color of the biological indicator on a regular basis, he would see the color of the dye change from the original color to the color of the dye in a basic solution and then back to the original color. The observer would likely be confused by the multiple color changes and might believe that the biological indicator is defective. The recognition of the previously unrecognized cause of the problem of dye reversion from leaching or diffusion of basic contaminants into the growth medium is one aspect of the method and the apparatus of the present invention.

The embodiments of the apparatus and the method of the present invention address the previously unrecognized cause of the problem of dye reversion through the use of a dual buffer system. Although single buffer systems have been previously used in biological indicators, the need for a dual buffer system was not previously recognized. The present invention therefore includes both the recognition of a cause of the problem as well as the solution for the problem.

Although the dual buffer system of the present invention is described in the context of a dual buffer system for biological indicators where the dual buffer system includes a small amount of high pH buffer and a large amount of low pH buffer, it is to be understood that the dual buffer system has broad application, and the concept of the dual buffer system is not meant to be limited to the embodiment of biological indicators. The broader application of dual buffer systems will be described in more detail after the description of the more specific application to biological indicators.

The single buffer system previously used provided some stability to the biological indicator to minimize the number of false positives due to small amounts of acid impurities. For example, if a small amount of acid were present in the atmosphere in the sterilization system at the beginning of the sterilization process, the acid would be retained by the buffer system in the biological indicator with only a minimal pH change. The pH would not be shifted sufficiently to cause a change of color in the indicator dye in the biological indicator system.

The single buffer system stabilizes the pH in the system from both acidic and basic conditions. Choosing a single buffer with a $pK_a$ about 7 stabilizes the system at a pH of approximately 7. A pH of about 7 is suitable for microorganism growth.

With the dual buffer system according to embodiments of the method and the apparatus of the present invention, one buffer system has a pH range sufficient to allow the indicator dye to change color if acid is generated from metabolism of the growth medium by bacteria. The second buffer controls the pH after the dye has changed color so that the pH of the system is not significantly shifted by the basic impurities, causing the indicator dye to revert to its original color. The dual buffer system overcomes the previously unrecognized cause of the problem of color reversion of the indicator dye.

FIG. 1 depicts a cross-sectional view of a sterility indicator 10 suitable for use with the dual buffer system according to the apparatus and method of the present invention. The structure of the sterility indicator 10 of FIG. 1 is somewhat similar to the SCBI described in U.S. Pat. No. 5,552,320, hereby incorporated by reference, except that the sterility indicator of FIG. 1 has only one inner container rather than the two inner containers of the SCBI of U.S. Pat. No. 5,552,320. A wide variety of both biological indicators and self-contained biological indicators (SCBIs) are suitable for use in the method and the apparatus of the embodiments of the invention, and the example of the sterility indicator 10 of FIG. 1 is not meant to be limiting on the embodiments of either the method or the apparatus of the present invention.

Returning to FIG. 1, transparent vial 12 has liquid impermeable walls 14 and open end 16. A medium ampoule 20 inside the transparent vial 12 contains a liquid culture medium 22. The medium ampoule 20 is sealed, and the interior of the medium ampoule 20 is not in fluid communication with the interior of the transparent vial 12 until the medium ampoule 20 is opened. A carrier 24 is located at a bottom of the transparent vial 12 at an end of the transparent vial 12 opposite the open end 16. The carrier 24 is made of a material such as TYVEK™, stainless steel, fiberglass, and the like. The carrier 24 may be a porous substrate, a non-porous substrate, an absorbent substrate, or a non-absorbent substrate. The carrier can be a disk or a strip or have another suitable shape. If the carrier 24 retains or absorbs disinfectant or sterilant, another chemical may be needed in the sterility indicator 10 to neutralize or decompose the sterilant or disinfectant.

The carrier 24 is inoculated with a predetermined concentration of viable spores or other microorganisms. One suitable microorganism is *Bacillus stearothermophilus* spores, although other suitable microorganisms may also be used with the apparatus and method of embodiments of the invention. *Bacillus stearothermophilus* is normally used as a biological indicating microorganism with steam sterilization processes. *Bacillus subtilis* var. *niger* is used as a biological indicating microorganism with ethylene oxide and dry heat sterilization processes. Either *Bacillus stearothermophilus* or *Bacillus subtilis* var. *niger* may be used as biological indicating microorganisms in the STERRAD® process depending on the carrier and how easily the sterilant can diffuse into the biological indicator. The STERRAD® process utilizes a combination of hydrogen peroxide and plasma. Other microorganisms are suitable for use with the method and the apparatus of the embodiments of the invention, and the microorganisms described above are not meant to be limiting.

The open end 16 of the transparent vial 12 is covered by a gas or vapor-permeable, microorganism-impermeable closure sheet 26. The closure sheet 26 can be made of a nonwoven fabric such as TYVEK™, CSR wrap, or other suitable material. CSR wrap is nonwoven polypropylene. TYVEK™ is a tradename for spun-bonded polyethylene. In an exemplary embodiment, the closure sheet 26 is made of a nonwoven polyolefin. Alternatively, the closure sheet 26 can be any kind of hydrophobic filter which is gas or vapor permeable but impermeable to microorganisms. The closure sheet 26 is held in place by a cap 28. The cap 28 snaps over the open end 16 of the transparent vial 12 and is held in place by friction. A chemical indicator 30 is preferably located at a top of the cap 28 and is held in place on the end of the cap 28 by a plurality of flexible tabs 32. At least one hole 34 is located in the cap 28. The hole 34 allows germicide to enter the cap 28.

The culture medium 22 in the medium ampoule 20 contains dye which undergoes a visible change with a change of pH in the culture medium 22. The visible change in the dye with a change in pH can be detected through the walls 14 of the transparent vial 12. As used in the present specification and claims, "transparent" is the quality of the walls 14 that permits visible changes in the color of the dye in the culture medium 22 to be detected from the outside. The walls 14 of the transparent vial 12 may therefore be translucent rather than transparent. Further, in some embodiments, the walls 14 of the transparent vial 12 are opaque, and there is a transparent or translucent window in the transparent vial 12 to allow for observation of the color change of the dye. Alternatively, all or a portion of the cap 28 may be transparent or translucent.

The transparent vial 12 is preferably made of a flexible plastic which is resistant to hydrogen peroxide. Polypropylene is an exemplary plastic for use in fabricating the transparent vial 12. Although it is not necessary that the cap 28 be transparent or translucent, in an exemplary embodiment, the cap 28 is transparent or translucent and is made of the same plastic as the transparent vial 12. In other embodiments, the cap 28 is made from a material which is different than the material from which the transparent vial 12 is made.

The medium ampoule 20 is made of a frangible material such as glass. In an embodiment, the walls 14 of the transparent vial 12 are deformable so that the medium ampoule 20 can be opened (by crushing, for example) without breaking the walls 14 of the transparent vial 12.

The chemical indicator 30 is any indicator which indicates exposure to a sterilant. One suitable chemical indicator 30 for oxidative sterilants such as hydrogen peroxide is a chromate coated aluminum alloy disk coated with Bordeaux Red dye, as described in detail in U.S. Pat. No. 5,942,438, hereby incorporated by reference. Bordeaux Red dye has the tradename Aluminum Bordeaux RL. Other chemical indicators 30 are suitable for use with the apparatus and the method of the embodiments of the present invention. The chemical indicator 30 of U.S. Pat. No. 5,942,438 changes color from red to a yellow/gold color when exposed to an oxidation-type sterilant. The chemical indicator 30 of U.S. Pat. No. 5,942,438 can therefore be used as a means of determining whether or not the sterility indicator 10 has been exposed to an oxidative sterilant. Other forms of chemical indicators 30 can be used to indicate exposure to sterilants such as steam, heat, or ethylene oxide. The chemical indicator 30 is optional and is not necessary for the embodiments of the apparatus or the method of the present invention.

Figure 2:
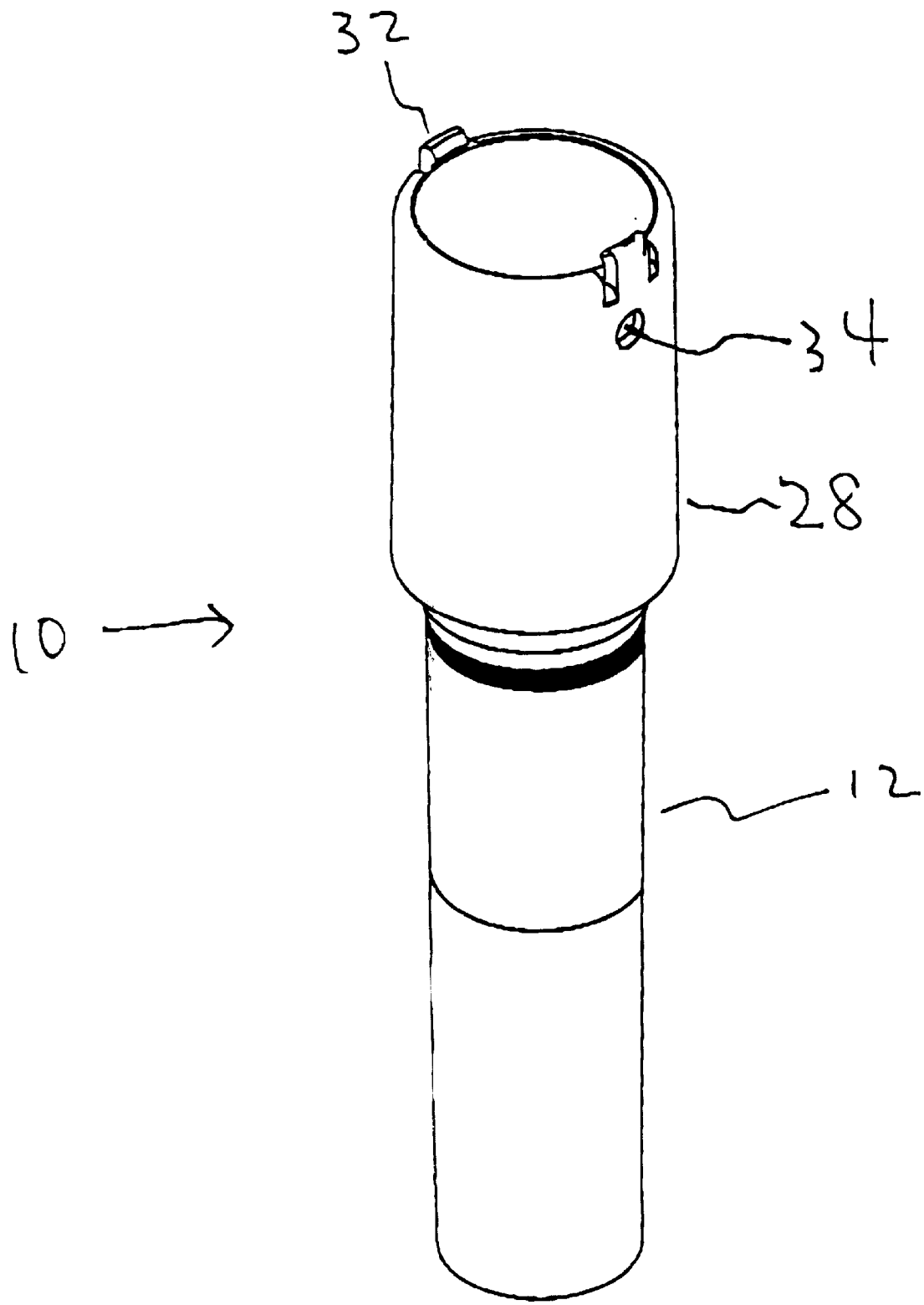
FIG. 2 is a perspective view of the self-contained biological indicator of FIG. 1.

FIG. 2 shows a perspective view of the sterility indicator 10 of FIG. 1, showing in more detail how the cap 28 fits onto the transparent vial 12. FIG. 2 also shows more clearly the tabs 32 which hold the chemical indicator 30 in place on the top of the cap 28. FIG. 2 also shows the hole 34 in the cap 28. The hole 34 allows sterilant or germicide to enter the interior of the sterility indicator 10.

The medium ampoule 20 of FIG. 1 contains a culture medium 22 and a dye. One suitable culture medium 22 is Tryptic Soy Broth (available from SGM Biotech, Bozeman, Mont.). The dye has a first color at high pH and a second color at low pH, so that the color in the culture medium 22 changes if the pH changes from a high pH range to a low pH range during incubation of the sterility indicator 10 due to generation of acidic byproducts from the metabolism of the culture medium 22 by the surviving microorganisms. In other embodiments, the dye is in the transparent vial 12 outside of the medium ampoule 20. The dye is then brought into contact with the culture medium 22 when the medium ampoule 20 is opened.

The sterility indicator 10 is placed in the sterilizer with the equipment to be sterilized. The equipment to be sterilized and the sterility indicator 10 are then subjected to a sterilization cycle. The sterilization cycle may be any suitable sterilization cycle, including, but not limited to, sterilization cycles with a disinfecting or sterilizing agent such as heat, steam, ethylene oxide, plasma, hydrogen peroxide, a combination of hydrogen peroxide and plasma, chlorine dioxide, ozone, peracetic acid, formaldehyde, or any other suitable sterilization process. During the sterilization cycle, the steam or germicide gas or vapor may enter the sterility indicator 10 through the hole 34 in the cap 28. The germicide gas or vapor can be a disinfectant or a sterilant. In the context of this application, disinfectant is to be understood to be a germicide which kills microorganisms in the vegetative stage but does not necessarily kill spores. A sterilant is to be understood to be a germicide which kills all microorganisms, including spores. Because the closure sheet 26 on the open end 16 of the transparent vial 12 is vapor-permeable or gas-permeable, the germicide gas or vapor can penetrate the closure sheet 26. The microorganisms on the carrier 24 are therefore exposed to the sterilizing atmosphere during the sterilization cycle. If heat is used as the sterilization cycle, the sterility indicator 10 is subjected to the same heat conditions as the equipment to be sterilized.

After completion of the sterilization cycle, the sterility indicator 10 is removed from the sterilizer, and the medium ampoule 20 is opened to expose the microorganisms on the carrier 24 to the culture medium 22. The medium ampoule 20 may be opened in any suitable manner. One method of opening the medium ampoule 20 is to deform the walls 14 of the transparent vial 12 to crush the medium ampoule 20, though any suitable method of opening the medium ampoule 20 may be used.

The sterility indicator 10 is then placed in a conventional incubator at a temperature and for a time suitable for growing the microorganism in the culture medium. For example, with *Bacillus stearothermophilus* spores, incubation of 48 hours or more at a temperature of 58° C. is suitable for growth of the microorganism.

If the microorganism grows during the incubation cycle, the metabolism of the culture medium 22 by the microorganism produces acidic byproducts, lowering the pH of the culture medium 22. The change in pH causes a change in color of the dye in the culture medium 22. A change in the color of the dye during incubation of the sterility indicator 10 indicates that sterilization was not complete. The absence of a color change confirms that the sterilization cycle was effective. In alternative embodiments, the change in pH may be detected with a pH meter, pH paper, or by any suitable pH measuring method.

Figure 3:
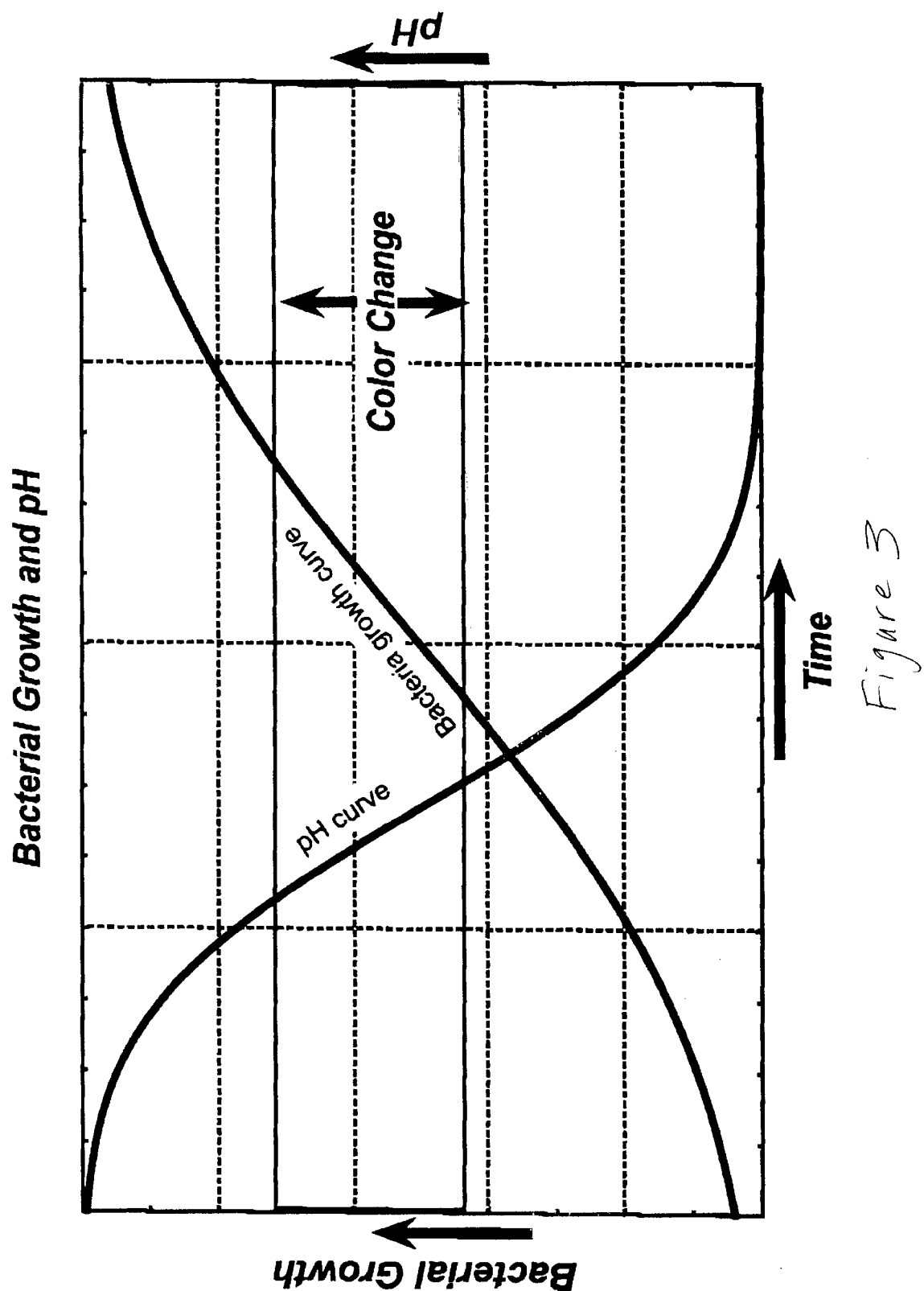
FIG. 3 is a graph showing bacterial growth (left hand axis) and pH (right hand axis) versus time in a culture medium in a biological indicator with a dual buffer system according to embodiments of the method of the present invention.

FIG. 3 shows graphs of the growth curve of the bacteria versus time (left hand scale) and the curve of pH versus time (right hand scale) for a typical sterility indicator 10. As shown in FIG. 3, the pH in the growth medium 22 changes from a high pH range to a low pH range during the course of the incubation due to generation of acid byproducts from the metabolism of the culture medium 22 by the bacteria. If Bromcresol Purple dye is used as the indicator dye, the Bromcresol Purple dye changes from purple above a pH of about 6.8 to yellow below a pH of about 5.2. A change of color from purple to yellow with a sterility indicator 10 containing Bromcresol Purple dye in the culture medium 22 therefore indicates bacterial growth. The example of Bromcresol Purple is used to illustrate the method, and the embodiments of the apparatus and the method of the present invention are not limited to Bromcresol Purple dye. (Bromcresol Purple dye is also known as Bromocresol Purple dye.)

At the start of the incubation period, even a small amount of acid contamination due to the presence of carbon dioxide or other acidic impurities could shift the pH enough to change the color of the dye. For example, in a system with Bromcresol Purple, a shift in pH from 7 to about 6.0 would be sufficient to cause the Bromcresol Purple indicator to start to change from the purple color. A buffer is therefore commonly added to the culture medium 22 to reduce the sensitivity to false positives as a result of small amounts of acidic contaminants. In order to make the system as sensitive as possible and to make the response of the system as fast as possible, only a small amount of buffer is used.

If base were to be introduced into the culture medium 22 after the pH in the culture medium 22 had decreased sufficiently for the dye to change color, the pH in the culture medium 22 could increase sufficiently to change the color of the dye back to the original color. In the example of Bromcresol Purple, a shift in pH from about 5.2 to above about 6 would change the color of the Bromcresol Purple dye from yellow at low pH to purple at high pH, falsely indicating that no bacterial growth had occurred.

Although the dye reversion would not be an issue if the sterility indicator 10 were monitored regularly, the sterility indicators 10 are sometimes not monitored until the end of the seven day incubation period, long enough for dye reversion to take place. In such a case of dye reversion, even though a positive readout has occurred sometime during the seven day incubation period, a subsequent readout would show that the original color had returned, indicating a shift in pH toward the original pH value. The reading is then unreliable, because it can lead to confusion and uncertainty, in some cases leading to bacterial growth being seen as no growth.

It has been found that a basic contaminant leaches or diffuses out of certain batches of transparent vial 12, causing a change in pH to above 6.0, with a resulting color change of the Bromcresol Purple dye back to purple during the seven day incubation period, a color reversion. The color reversion would falsely indicate no bacterial growth. Color reversion is, of course, not limited to Bromcresol Purple dye, and the example of Bromcresol Purple dye is illustrative only. The recognition of the reasons for the color reversion from leaching or diffusion of basic contaminants is a recognition of a previously unrecognized cause of a problem and is a part of the present invention.

Dual Buffer System

A dual buffer system for sterility indicators 10 has been developed which eliminates the problem of color reversion while retaining the speed and sensitivity of the determination of the effectiveness of the sterilization process. Returning to FIG. 3, the growth medium 22 contains a small amount of buffering agent. The buffer stabilizes the pH somewhat against small additions of ions that can change the pH of the solution, which could change the color change of the indicator. Potassium phosphate, dibasic ($K_2HPO_4$) is an exemplary buffer. A potassium phosphate, dibasic buffer maintains the starting pH level at about 7.0, a pH which is suitable for bacterial growth.

During bacterial growth, the metabolic acids and by-products act to reduce the pH. When the buffering capacity of small amount of buffer in the growth medium 22 is overcome, the pH value drops. If Bromcresol Purple dye is used as the indicator dye, the indicator dye changes color at a pH level around 5.2 or below, giving visible indication of growth. The incubation and readout period is 2–7 days. If the color change is observed during incubation at any time before the end of the second day, the result is recorded as positive growth of the biological indicator. If the user is unable to read the sterility indicator 10 after the second day, the sterility indicators may be kept up until seven days until read.

In order to prevent reversion, one approach would be to ensure that the contaminant level in the polypropylene transparent vials 12 is kept very low. However, the amount of basic contaminants necessary to shift the pH and cause reversion in the present system is small, because of the small amount of buffer in the present system. The one buffer system is not effective to buffer the medium at the lower pH range. If an occasional lot of polypropylene vials contained an basic contaminant which could leach out of the polypropylene, dye reversion could occur, and the contaminated lot of vials would have to be discarded.

However, if basic contamination is introduced, such as by leaching or diffusion of ions from the material of the transparent vial 12, the pH may shift back again toward neutral. If the pH rises sufficiently, the indicator dye begins to return to the original color, causing confusion or even giving a false negative reading. Although the amount of buffer in the culture medium 22 could be increased to lessen the possibility of this color reversion, increasing the amount of buffer would decrease the sensitivity and speed of the method.

According to an embodiment of the method of the invention, adding a second buffer with a buffering range near the end point of the indicator acts to stabilize the pH in the region of the end point. If Bromcresol Purple is used as the indicator dye, the end point of the system is in the pH 4–5 range, where the dye is yellow. Rather than adding more buffer having a $pK_a$ of about 7, which would decrease the sensitivity of the system, a second buffer with a $pK_a$ of about 4–5, near the end point, is added to the system. The second buffer with the $pK_a$ of about 4–5 tends to hold the pH steady in the pH 4–5 range. The second buffer having a $pK_a$ in the 4–5 range stabilizes the system in the pH range of 4–5 when the bacterial acid lowers the pH into this range. Because the second buffer stabilizes the system in the pH 4–5 range, basic contaminants which leach or diffuse into the system are neutralized by the second buffer, and the pH remains in the pH 4–5 range. Because only a small amount of the first buffer in the pH 7 range is used, the system retains the speed and sensitivity of the indicator readout. The larger quantity of buffer having a pKa near the pH of the end point stabilizes the system after the end point is reached, minimizing the possibility of dye reversion while not decreasing the sensitivity of the system.

The advantages of the dual buffer system are that it:
1. preserves the speed and sensitivity of the readout while
2. increasing the readout stability and reliability.

The dual buffer system thus eliminates the trade-off between sensitivity and reliability as in the single buffer system.

If Bromcresol Purple is used as the indicator dye, the dye changes color from purple to yellow in the pH range of about 6.8 to about 5.2. A suitable dual buffer system for the system with Bromcresol Purple includes a relatively small amount of buffer with a $pK_a$ in the range of about 7 and a relatively large amount of buffer with a $pK_a$ in the range of about 4–5.

The larger amount of buffer with a $pK_a$ in the range of 4–5 does not affect the sensitivity of the system, because the color change indicating bacterial activity occurs in the pH range of about 5–6, outside the buffering range of the buffer with a $pK_a$ of 4–5. The small amount of buffer with a $pK_a$ of about 7 therefore protects against false positives, while the larger amount of buffer with a $pK_a$ of about 4–5 protects against shifts in pH due to leaching or diffusion of base, eliminating color reversion of the dye.

There are a variety of dual buffer systems and dyes which are suitable for the sterility indicator 10 operating in the pH range of 7 at the start and about 4–5 at the end. Phosphate buffer ($KH_2PO_4$ and $K_2HPO_4$) with a pKa of 7.0 is a suitable buffer for controlling the pH at the start of the incubation period at the pH of approximately 7.0. The pH of about 7 is suitable for bacterial growth. The phosphate buffer is preferably at a concentration of approximately 0.2 grams/liter (about 1 mmolar).

Table 1 shows some suitable buffer systems with $pK_a$'s in the range of 4–5. The buffer systems with $pK_a$'s in the 4–5 range are suitable for preventing dye reversion.

TABLE 1

Buffer Systems Having pKa's in the 4–5 Range

| Chemical | Concentration | $pK_a$ |
| --- | --- | --- |
| Citric Acid | 0.01–0.1 M | 4.76 |
| Sodium Acetate | 0.01–0.1 M | 4.76 |

As seen in Table 1, the buffer having a $pK_a$ in the 4–5 range is present in a concentration of about 0.01–0.1 molar, compared to approximately 1 millimolar for the buffer with a $pK_a$ of about 7. The buffer with a $pK_a$ of 7 is therefore present in a concentration of about $1/10$ to $1/100$ the concentration of the buffer with a $pK_a$ in the 4–5 range. By using a small amount of buffer with a $pK_a$ of 7, the sensitivity of the method is retained.

Table 2 shows a series of dyes which are suitable for use in the system shown in FIG. 3. All of the dyes have a pH range of about 4–7.

TABLE 2

Suitable Dyes

| Dye | Concentration | Color Change | pH Range |
| --- | --- | --- | --- |
| Bromcresol Purple | 8–12 mg/l | Yellow-Purple | 5.2–6.8 |
| Chlorophenol Red | 8–12 mg/l | Yellow-Purple | 4.8–6.6 |
| Chrysoidin | 8–12 mg/l | Orange-Yellow | 4.0–7.0 |
| Alizarin | 8–12 mg/l | Yellow-Red | 5.6–7.2 |

The dual buffer system is not limited to the embodiment of having a pH change from 7 to a range of 4–5, as previously described. The dual buffer system can be applied to any system in which a pH change occurs. In the broader concept of the dual buffer system, the dual buffer system is applicable to any system in which a change in pH from a first pH range to a second pH range occurs, where the pH change is indicative of a result. In the present case, the pH change indicates bacterial growth and the ineffectiveness of the sterilization cycle.

In the broad concept of the dual buffer system and method, the dual buffer system contains a first buffer which has a $pK_a$ in the first pH range and a second buffer which has a $pK_a$ in the second pH range. The first buffer stabilizes the pH in the region of the first pH range, and the second buffer stabilizes the pH in the second pH range. The relative amounts of the two buffers are chosen depending on whether it is important for the system to be sensitive in the region of the first pH or the second pH. If it is important to have sensitivity in the region of the first pH, a small amount of the first buffer which has a $pK_a$ close to the first pH is used. Similarly, if it is important to have sensitivity in the region of the second pH, a small amount of the second buffer which has a $pK_a$ close to the second pH is used. The relative amounts of the first buffer and the second buffer are therefore chosen to optimize the relative sensitivity of the system in the region of the first pH range and the second pH range.

The two buffers are chosen depending on the pH range of the pH-sensitive dye. One buffer is chosen so that the $pK_a$ of the buffer is around or higher than the high end of the pH range of the dye. The second buffer is chosen so that the $pK_a$ of the buffer is around or lower than the low end of the pH range of the pH-sensitive dye. The $pK_a$'s of the two buffers therefore bracket the pH range of the dye. The relative quantities of the two buffers are selected so that a lower concentration of buffer is used at the end of the pH range of the dye where more sensitivity is desired. The dye changes color from a first pH range to a second pH range. The first pH range is the pH around or higher than the high end of the pH range of the dye. The second pH range is the pH of the buffer around or lower than the pH range of the dye.

The embodiments of the method of the present invention for minimizing or eliminating dye reversion by using a dual buffer system are not limited to self-contained biological indicators as shown in FIG. 1. For example, the embodiments of the method are applicable to a wide range of biological indicators. In particular, the dual buffer system can be used with conventional biological indicator carriers. It can also be applied to the biological indicator carriers used for liquid disinfectant or sterilant, such as glutaraldehyde, performic acid, peracetic acid, hydrogen peroxide, formaldehyde, ortho-phthalaldehyde, or hypochlorite salts such as sodium hypochlorite. When the method is applied to these biological indicators, the carrier, after treatment with liquid, gas, or vapor disinfectant or sterilant, is placed into a culture medium 22 which contains a dual buffer system. The dual buffer system according to embodiments of the method of the present invention will eliminate or at least minimize the possibility of dye reversion, when conventional biological indicator strips are incubated in the culture medium which contains the dual buffer system according to embodiments of the present invention.

The dual buffer system is also applicable to a wide variety of self-contained biological indicators (SCBIs) such as the SCBI of FIGS. 1 and 2, as well as a wide variety of other SCBIs. In embodiments of the method of the present invention, the conventional culture medium 22 which is utilized in many SCBIs is augmented or supplemented with a dual buffer system according to embodiments of the present invention.

A culture medium 22 according to embodiments of the invention contains a nutrient broth, the dual buffer system, and a pH-sensitive dye. In some embodiments, the dual buffer system and/or the pH-sensitive dye are separate from the nutrient broth. The nutrient broth, the dual buffer system, and the pH-sensitive dye are brought into contact with each other when the medium ampoule 20 is opened.

Although the dual buffer system has been described with respect to a hydrogen peroxide/plasma sterilization system, the dual buffer system can be applied to any system where a pH change occurs. In particular, the dual buffer system can be applied to indicators for sterilization with ethylene oxide, heat, steam, hydrogen peroxide, plasma, a combination of hydrogen peroxide and plasma, glutaraldehyde, peracetic acid, performic acid, formaldehyde, ortho-phthaldehyde, hypochlorite salts such as sodium hypochlorite, ozone, chlorine dioxide, or a variety of germicides.

Various modifications and alterations of this invention will be apparent to those skilled in the art without departing from the scope and spirit of this invention. It is to be understood that the invention is not limited to the embodiments disclosed therein, and that the claims should be interpreted as broadly as the prior art allows.

What is claimed is:

1. A self-contained biological indicator comprising;
   a carrier with viable microorganisms on the carrier;
   a container containing said carrier therewithin, wherein at least a portion of said container is transparent and wherein said container comprises an opening which is covered with a gas or vapor permeable but microorganism impermeable barrier;
   at least one openable enclosure inside said container, wherein said enclosure contains a culture medium which is capable of supporting growth of the viable microorganisms;
   a dye which changes color with a change in pH from a first pH range to a second pH range; and
   a dual buffer system, wherein said dual buffer system comprises a first buffer having a first $pK_a$ and a second buffer having a second $pK_a$ wherein said first $pK_a$ and said second $pK_a$ are within said first pH range and said second pH range respectively.

2. The self-contained biological indicator of claim 1, wherein said carrier is selected from the group consisting of a porous substrate, a non-porous substrate, an absorbent substrate, and a non-absorbent substrate.

3. The self-contained biological indicator of claim 1, wherein said gas or vapor permeable but microorganism impermeable barrier is a nonwoven polyolefin.

4. The self-contained biological indicator of claim 1, wherein said viable microorganism comprises a biological indicating microorganism for a disinfection or sterilization process.

5. The self-contained biological indicator of claim 1, wherein said openable container comprises a breakable glass ampoule.

6. The self-contained biological indicator of claim 1, wherein said dye comprises Bromcresol Purple.

7. The self-contained biological indicator of claim 1, wherein said first buffer comprises at least one phosphate salt.

8. The self contained biological indicator of claim 1, wherein said second buffer comprises at least one acetate salt.

9. The self contained biological indicator of claim 1, wherein said at least one acetate salt is sodium acetate.

10. The self-contained biological indicator of claim 1, wherein said dual buffer system comprises a lower concentration of buffer having a $pK_a$ in said first pH range than buffer having a $pK_a$ in said second pH range.

11. The self-contained biological indicator of claim 1, further comprising a cap with at least one opening above said barrier, whereby gas or vapor can diffuse into said container through said hole and said barrier.

12. The self-contained biological indicator of claim 1, further comprising a chemical indicator for indicating exposure of said self-contained biological indicator to a disinfection or sterilization process.

* * * * *